United States Patent [19]
Utsumi et al.

[11] Patent Number: 5,441,489
[45] Date of Patent: Aug. 15, 1995

[54] CATHETER WITH BODY TEMPERATURE GLASS TRANSITION REGION

[75] Inventors: Atsushi Utsumi; Yukio Morita, both of Itami; Tamotsu Kaide; Kazuo Onishi, both of Amagasaki; Shunichi Hayashi, Chita, all of Japan

[73] Assignees: Mitsubishi Cable Industries, Ltd., Amagasaki; Mitsubishi Jukogyo Kabushiki Kaisha, Tokyo, both of Japan

[21] Appl. No.: 623,414
[22] PCT Filed: Apr. 11, 1990
[86] PCT No.: PCT/JP90/00488
§ 371 Date: Feb. 14, 1991
§ 102(e) Date: Feb. 14, 1991
[87] PCT Pub. No.: WO90/11793
PCT Pub. Date: Oct. 18, 1990

[30] Foreign Application Priority Data

Apr. 13, 1989 [JP] Japan ................ 1-43371 U
Apr. 13, 1989 [JP] Japan ................ 1-43372 U

[51] Int. Cl.$^6$ ........................................... A61M 25/00
[52] U.S. Cl. ................................. 604/280; 604/281; 604/282
[58] Field of Search ............ 604/95, 264, 280–283; 128/772, 656–658

[56] References Cited

U.S. PATENT DOCUMENTS

| | | | |
|---|---|---|---|
| 2,472,485 | 6/1949 | Krippendorf | 604/282 |
| 3,416,531 | 12/1968 | Edwards | 604/95 |
| 3,485,234 | 12/1969 | Stevens | 604/281 |
| 3,498,286 | 3/1970 | Polanyi et al. | 604/282 |
| 3,618,614 | 11/1971 | Flynn | 604/282 |
| 4,248,234 | 2/1981 | Assenza et al. | 604/282 |
| 4,411,655 | 10/1983 | Schreck | 604/281 |
| 4,425,919 | 1/1984 | Alston, Jr. et al. | 604/282 |
| 4,690,175 | 9/1987 | Ouchi et al. | 604/282 |
| 4,739,768 | 4/1988 | Engelson | 604/282 |
| 4,817,613 | 4/1989 | Jaracewski et al. | 604/282 |
| 4,840,622 | 6/1989 | Hardy | 604/280 |
| 4,846,812 | 7/1989 | Walker et al. | |
| 4,886,506 | 12/1989 | Lovegren et al. | 604/282 |
| 4,899,787 | 2/1990 | Ouchi et al. | 604/282 |
| 4,994,047 | 2/1991 | Walker et al. | 604/264 |
| 5,019,057 | 5/1991 | Truckai | 604/282 |
| 5,045,072 | 9/1991 | Castillo et al. | 128/658 |
| 5,171,232 | 12/1992 | Castillo et al. | 604/280 |

FOREIGN PATENT DOCUMENTS

| | | |
|---|---|---|
| 867144 | 2/1953 | Germany . |
| 2140755 | 2/1973 | Germany . |
| 54-8036 | 4/1979 | Japan . |
| 61-293214 | 12/1986 | Japan . |

*Primary Examiner*—C. Fred Rosenbaum
*Assistant Examiner*—Mark Bockelman
*Attorney, Agent, or Firm*—Varndell Legal Group

[57] ABSTRACT

A catheter consists of a torque transmitting portion which has rigidity sufficient for torque transmission and a flexible portion made of a material having a glass transition temperature for giving rigidity before insertion and flexibility after insertion. The torque transmitting portion maintains torque transmitting ability before, during and after insertion. The flexible portion maintains appropriate rigidity before and during insertion, which enables easy insertion, and gains flexibility after insertion by the body heat, which avoids hurting of the vulnerable insertion walls. Further, the torque transmitting portion may have a structure wherein a reinforcement of a coil or a braid of linear metal wires, specifically flat rectangular wires, is attached thereto to afford torque transmitting ability. Catheters having various functions and structures can be easily manufactured by extrusion-molding, or the like.

16 Claims, 6 Drawing Sheets

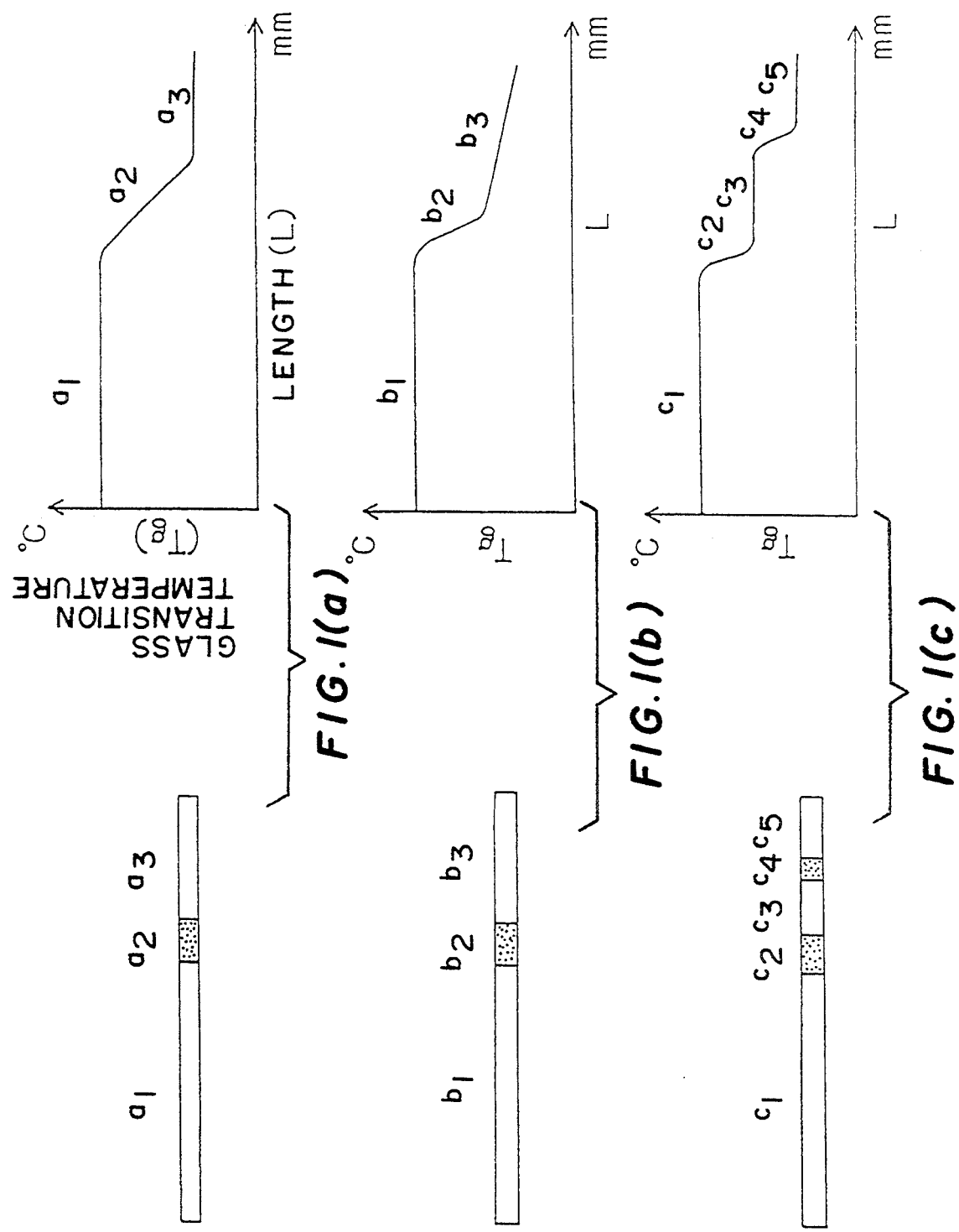

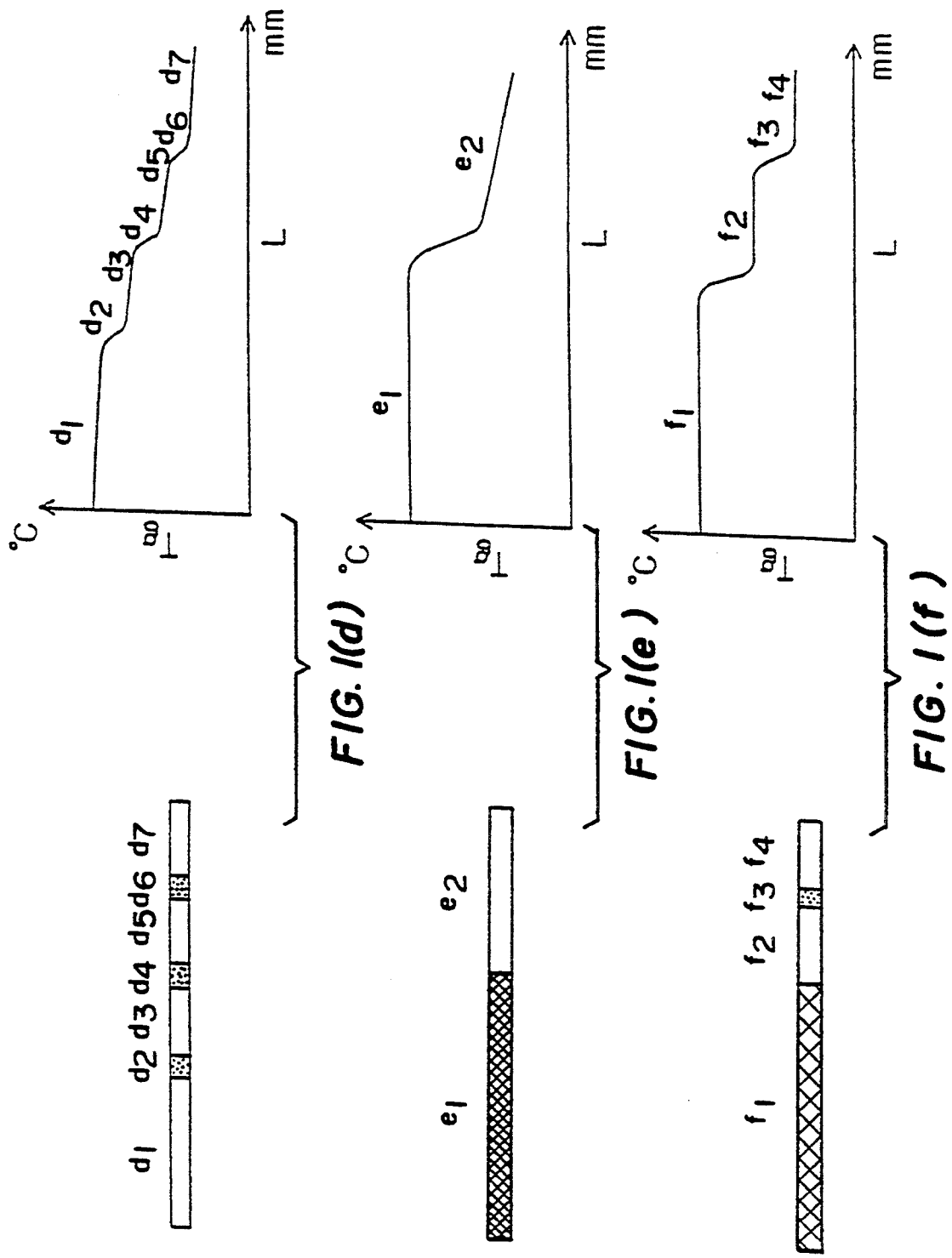

CATHETER WITH BODY TEMPERATURE GLASS TRANSITION REGION

FIELD OF THE INVENTION

The present invention relates to a catheter inserted into bodies of animals including humans for treatment, diagnosis or other purposes.

BACKGROUND ART

Catheters are designed for-insertion into vessels including coronary arteries, tubes including tracheas, uterine tubes and ureters, and internal organs so as to permit injection or evacuation of fluids or to maintain the openness of a passageway.

Flexible catheters generally used are made of a resilient or elastic material throughout the whole length. While such flexible catheters are inserted into passageways or body cavities of relatively simple structures without any difficulty, they are not smoothly inserted into those of complicated structures due to their total flexibility.

Our study has proved that a catheter, which is smoothly inserted into the body should possess adequate flexibility and elasticity on its insertion end (hereinafter referred to as flexible portion), and rigidity sufficient for effective torque transmission on its base (hereinafter referred to as torque transmitting portion).

The rigid torque transmitting portion of a catheter is useful for easy and smooth insertion of the flexible portion into the vicinity of the target regions such as vessels and internal organs. Furthermore, the torque transmitting portion efficiently transmits torque, which is generated by rotating a handle of the catheter (non-inserted portion adjacent to the torque transmitting portion), to the flexible portion, so that the running direction of the flexible portion is appropriately adjusted from the vicinity of the target regions to the final target portion.

On the other hand, appropriate flexibility is required on the flexible portion. Otherwise, the flexible portion would not easily follow the movement of the torque transmitting portion corresponding to the torque generated by rotation of the handle into a direction and at an angle desired when adjusting the direction and angle of the inserted catheter after insertion or during insertion of the catheter, or it may hurt tissues of vessels or internal organs upon insertion thereof.

Heretofore, catheters having both the torque transmitting ability of the torque transmitting portion and flexibility of the flexible portion have been proposed. For example, Japanese Published Patent Application No. Sho 54-8036, "Plastic tube used for medical purposes" discloses a catheter having a flexible portion and a rigid portion. Although appropriate flexibility is required on the flexible portion as described above, consistent flexibility of the flexible portion before insertion causes undesirable bent thereof due to friction against the wall of insertion guide tubes or the wall of passageways in the body during insertion to the target region, giving rise to difficulty in inserting smoothly. Appropriate rigidity is desirable on the flexible portion for easy and smooth insertion. The rigid flexible portion may, however, hurt the passageways. In other words, the flexible portion should possess conflicting properties, i.e., flexibility and rigidity.

The object of this invention is accordingly to provide an improved catheter, which is easily and smoothly inserted into the body, has efficient torque transmitting ability to a flexible portion, and does not hurt inside of the body by the flexible portion.

DISCLOSURE OF THE INVENTION

The above object is achieved by a catheter of the invention including a torque transmitting portion (or section) which has rigidity sufficient for torque transmission, and a flexible portion (or section) made of a material having an optimum glass transition temperature for giving appropriate rigidity before insertion and flexibility to the flexible portion after insertion.

The catheter of the invention is easily and smoothly inserted because of proper rigidity of both the torque transmitting portion and the flexible portion. After being inserted, the flexible portion is warmed by the body heat and becomes sufficiently flexible so as not to hurt the insertion wall and to favorably respond to a torque transmitted from the torque transmitting portion.

The catheter of the invention means any of various tubular medical devices inserted into the body for diagnosis, treatment,or any other purposes. Catheters of the invention have various functions according to their purposes and may be single lumen tubes used for evacuating and injecting fluids or guiding another catheter or a guide wire, or multi-lumen tubes used for evacuating and injecting .fluids, measuring the temperature or blood pressure, performing a blood test or chemical analysis, or acting as an endoscope, a laser fiber or a balloon. They are applicable to any of circulatory, respiratory, digestive, urinary, and generative systems.

As stated above, the catheter of the invention basically includes the torque transmitting portion and the flexible portion having both rigidity and flexibility. The length of the flexible portion depends on the structure of the catheter and its purposes, and is generally 5 through 500 mm. The flexible portion is connected to the torque transmitting portion directly or via a medium, or middle section if necessary. The medium preferably has the intermediate elastic modulus between those of the torque transmitting portion and the flexible portion before, during and after insertion. The catheter of said structure has the elastic modulus gradually and moderately changing from the torque transmitting portion to the flexible portion, and thus attains easy insertion and favorable torque transmission.

The two portions may be connected to each other with an adhesive or adhered to each other with heat. When the torque transmitting portion and the flexible portion are formed by successively extruding each material by an extruding method as described later, composition ratio of the two materials and the elastic modulus at the connection gradually vary. Thus, the connection has favorable functions as the medium.

In the catheter of the invention, the flexible portion consists of an organic polymer or polymers having the glass transition temperature the same as or near the body temperature of the target subject. The glass transition temperature is measured with a differential scanning calorimeter, at a temperature increase rate of 10° C./min and in a nitrogen atmosphere, based on JIS K7121-1987 "Method for measuring the transition temperature of plastics". When the material has two or more absorption peaks, the lowest temperature peak giving sufficient flexibility is determined as the glass transition temperature of the material. While the sufficient flexibility varies with the insertion target and the inserted portion, the elastic modulus is generally not greater than 50 kgf/mm², and more specifically not greater than 10 kgf/mm².

When organic polymers are warmed or heated, the elastic modulus generally shows a drastic drop at temperatures ten-odd degrees lower than the glass transition temperature and flexibility thereof increases. The organic polymer remains elastic and has appropriate rigidity as well as sufficient flexibility in a range from the glass transition temperature to temperatures ten-odd degrees higher. When the organic polymer is heated beyond the above temperature range, it loses rigidity and gains excessive flexibility. Excessive flexibility lowers response to a torque transmitted. The material of the flexible portion of the catheter has the glass transition temperature in a range of between $t_0-15$ and $t_0+15$, preferably $t_0-7$ and $t_0+7$, and more preferably $t_0-5$ and $t_0+3$ (where to is the body temperature of the target subject). For example, when the target is a humall (average temperature: 36.5° C.), the glass transition temperature is between 21.5° and 51.5° C., preferably 29.5° and 43.5° C., and more preferably 31.5° and 39.5° C.

When the glass transition temperature of the material composing the flexible portion is lower than $t_0-15$°C., the elastic modulus becomes too small and flexibility becomes too large immediately after the insertion by the warming by the body heat of the target, resulting in prevention of smooth insertion and delicate adjustment of a direction by a torque transmitted. On the other hand, when the glass transition temperature of the material is higher than $t_0+15$° C., the body heat does not sufficiently lower the elastic modulus and thereby the flexible portion may hurt the tube walls in the body. The material of the flexible portion is preferably those having the glass transition temperature in the above range and retaining the elastic modulus of 0.01 to 50 kgf/mm², specifically 0.1 to 10 kgf/mm² after warming by the body heat of the insertion target. The flexible portion may be composed of one material or two or more materials having different elastic moduli and glass transition temperatures as described later in Examples. In the latter case, the flexible portion preferably has the elastic modulus and glass transition temperature decreasing stepwise or gradually from the joint to the free end. The different materials may be connected to each other with an adhesive or adhered to each other with heat. A middle part, in which the composition gradually changes, is preferably formed between the torque transmitting portion and the flexible portion in a similar manner as described above.

The flexible portion of the catheter may be composed of any of various chemical compounds having the glass transition temperature and elastic modulus described above. For example, the material used is polyurethanes such as polyether polyurethane and polyester polyurethane. Preferable polyurethanes are those having $2 \times 10^5$ to $7 \times 10^5$ of the average molecular weight, those having 3 to 60% by weight of stoichiometrically calculated content (defined herein as crystallinity) of hard segments consisting of diisocyanate and short-chain glycols which are polyurethane materials, those having thermoplasticity of 160° to 210° C. of the fluidization temperature measured with viscoelasticity-measuring apparatus RMS-800 (Reometric), or those having the above-mentioned molecular weight, crystallinity and fluidization temperature. Polyurethanes described in Japanese Unexamined Published Patent Application No. Sho 61-293214, and Japanese Patent Applications No. Sho 63-244341 and No. Sho 63-260491 are also preferably used.

The flexible portion may be composed of a mixture of the above polyurethane and a thermoplastic organic polymer. The thermoplastic organic polymers may be polyolefins such as polyethylenes of various densities, polypropylenes, ethylenepropylene copolymers, and ethylene-vinyl acetate copolymers, polyvinyl chloride, polyamides, and various liquid crystal polymers. Among the above polymers, liquid polymers, specifically liquid crystal polymers (LCP) formed at relatively low temperatures are favorably used. More specifically, favorable LCPs are those extrusion-molded at low temperatures not higher than 280° C., preferably at 150° to 250° C., and more preferably at 170° to 220° C. Examples of such LCPs are thermotropic liquid polymers such as aromatic polymers and nonaromatic polymers including aliphatic components in the main chain, with preference given to thermotropic non-aromatic liquid crystal polymers. Commercially available ones are X7G (molding temperature: 240° C., Eastman Kodak), Novaculates [Mitsubishi Chemical Industry, specifically Novaculate E310 (molding temperature: 220° C.)], Lodrun [Unitika, specifically Lodrun LC-3000 (molding temperature: 230° C.)], and Idemitsu LCP [Idemitsu Petrochemical Industry, specifically Idemitsu LCP 100E (molding temperature: 240° )].

Polyurethane and LCP are mixed in the ratio of 5 through 120 of LCP to 100 of polyurethane, preferably 10 through 100 to 100, and more preferably 20 through 60 to 100 (here, the unit is parts by weight).

The torque transmitting portion of the catheter of the invention may have any structure and may be made of any material known in the pertinent field as long as it has required torque transmitting ability under the body heat of the target subject. The preferable mode of the torque transmitting portion is exemplified in the following.

The torque transmitting portion has the glass transition temperature at least 10° C., preferably 15° C., and more preferably 20° C. higher than the body temperature and elastic modulus of at least 50-kgf/mm², preferably at least 60 kgf/mm², and more preferably at least 70 kgf/mm². The material of the torque transmitting portion may be the same as those of the flexible portion with the above glass transition temperature and elastic modulus.

In specifying the glass transition temperature of the torque transmitting portion as well as the flexible portion, the glass transition temperature may change by any degrees from the torque transmitting portion to the flexible portion. For example, as shown in a preferred embodiment described later, the glass transition temperature may be virtually the same throughout the length of the torque transmitting portion and decreases from the border between the torque transmitting portion and the flexible portion to the insertion end of the flexible portion. The temperature may gradually decrease from the end of the torque transmitting portion to that of the flexible portion, or may gradually decrease from the middle region of the torque transmitting portion to the insertion end of the flexible portion. The glass transition temperature may decrease stepwise or in effect, gradually.

The torque transmitting portion may have a structure wherein a layer of organic polymers is reinforced with a coil or braid of metal wires as shown in FIGS. 2 through 4. The metal wire used may have a circular or flat rectangular cross section. Metal wires of flat rectangular cross section of a specified size described later give sufficient torque transmitting ability without making the reinforced portion, specifically braid, bulky, as compared with those of circular cross section of a similar size. The flat metal wires are thus preferable for preparing catheters of a small diameter with high torque transmitting ability. Since sufficient torque transmitting ability is given by reinforcing the torque transmitting portion with metal wires, be it circular or flat rectangular, high elastic modulus of the organic polymer layer of the torque transmitting portion is not necessarily essential. The organic polymer layer should rather possess functions preventing formation of thrombus, hurt to the insertion wall, and elution of metal wire components, which are possibly caused by exposure of the metal reinforcements in the body. The metal reinforcements are interposed between the organic polymer layers so as not to be exposed. When inner and outer organic polymer layers and the metal reinforcements are closely adhered, the higher torque transmitting ability can be obtained. While the inner layer for preventing exposure of the metal reinforcements may be very thin, e.g., 10 to 150 $\mu$m thick, the outer layer is required to have a thickness of at least 100 $\mu$m and preferably 200 to 1,000 $\mu$m, to cover the rough surface of the metal reinforcements which may cause formation of thrombus.

The metal wire of flat rectangular cross section may be any of those which give sufficient torque transmitting ability to the torque transmitting portion and do not adversely affect the human body. Wires preferably used have the elastic modulus of not less than 7,000 kgf/mm$^2$ and preferably not less than 10,000 kgf/mm$^2$ for giving appropriate flexibility to the torque transmitting portion. Examples of the wires of flat rectangular cross section include, for example, those prepared by rolling stainless steel, piano, tungsten, and nickel-titanium alloy wires into flat rectangular, those prepared by rolling those flat rectangular metal wires into those with smaller cross section, or the like.

The favorable aspect ratio (the ratio of width to thickness) of the wire is 1.5 through 20, and specifically 2 through 15. The favorable width of the wire is d/5 to d/50, and specifically d/7 to d/40 (d: outer diameter of metal reinforcements).

When a metal reinforcement, i.e., a coil or braid of wires, specifically those of flat rectangular cross section is prepared, each wire is so positioned that the inclination angle (acute angle) between each wire and the axis of the catheter becomes 20° to 80°, preferably 30° to 60°, and more preferably 40° to 55°. The number of the flat rectangular wire in the metal reinforcement is 0.1 to 20 and specifically 0.5 to 10 wires per 1 mm of the circumference (length: $\pi$d).

The cross sectional shape, size, and use of a flat rectangular wire are described above. Two or more thinner wires, preferably 2 to 10 thinner wires, may be used instead of one wire for the metal reinforcement. In this case, a bundle of 2 or more thin wires has the same aspect ratio and width as those of one flat rectangular wire described above. A bundle of thin wires gives better flexibility to the torque transmitting portion than one flat rectangular wire while high torque transmitting ability is maintained.

The torque transmitting portion reinforced with the above flat rectangular wire or a bundle thereof shows excellent performance as a torque transmitting tube, whether with or without the flexible portion.

The torque transmitting portion favorably includes an organic polymer tube, flat rectangular wire reinforcements, specifically a braid reinforcement, and organic polymer coating thereon. The reinforcements are covered with organic polymer coating, which is preferably as thin as possible for making the outer diameter of the catheter small. The coating material is preferably those capable of paint application, exemplified by, for example, vinyl chloride resin, polyethylenes, polyurethane coating, silicone rubber, fluororesin, with preference given to polyurethane coating.

The torque transmitting portion may include a temperature control mechanism for maintaining the elastic modulus of the organic polymer tube or the main body of the torque transmitting portion at a sufficient value for effective torque transmission. Details are described later according to FIG. 7.

The catheter of the invention possesses both rigidity and flexibility on the flexible portion and torque transmitting ability on the torque transmitting portion as described above. The preferable catheter should also fulfill other requirements: the inserted angle and direction are easily adjusted; and various operations are easily performed after insertion. While catheters of a small diameter are preferable when being inserted into small portions in the body, those of a large diameter are more practical for effectively injecting and evacuating fluids, opening the target region, and maintaining the openness. The flexible portion of the catheter has various shapes; for example, it is curved or hooked to facilitate easy arrival thereof by changing directions corresponding to the applied region. The catheters are preferably linear-shaped upon insertion, which affords smooth insertion as well as less probability of giving damage to the tissues in the body.

Accordingly, shape-memory materials are preferably used for preparing catheters. A specific shape is given to a catheter according to its use and application region. The catheter is linear-shaped before insertion and restored to a predetermined shape during insertion. Examples thereof include those wherein the flexible portion is warmed by the body heat and expands to a larger diameter or those wherein at least the flexible portion is restored to a predetermined shape such as curve-shape and hook shape by the body heat. The shape-memory materials may be any of those used for the flexible portion described above. Polyurethanes or mixtures of polyurethanes and LCPs having 30 through 50% by weight of crystallinity and 170 through 190 of fluidization temperature are especially preferable because of their excellent shape-memory ability and high processability.

As described above, the flexible portion of the catheter of the invention, which has having a specific glass transition temperature is warmed by the body heat and obtains sufficient flexibility. The catheter made of shape-memory materials is restored to a predetermined shape by the body heat. Thus, the catheter may include a temperature control mechanism for keeping the catheter from the influence caused by the body heat until it reaches the predetermined region. For example, a separate water path for circulating cooling water may be provided in the torque transmitting portion of the catheter so as to cool the catheter during insertion by circulating water. The water path may be provided in the flexible portion as well as in the torque transmitting portion so that cold or hot water runs in the water path to cool or warm the flexible portion as necessary for giving required rigidity or flexibility to the flexible portion, or restoring the flexible portion to the predetermined shape.

The flexible portion of the catheter may be provided with a treatment to give an opaque. Such a catheter is preferable when the current position of the catheter is traced with a photofluoroscope. The following three methods are generally used for giving an opaque.

(1) Barium sulfate ($BASO_4$) is added to the flexible portion to show an X-ray contrast.

(2) A gold or platinum ring or wire is attached to the flexible portion.

(3) A polymer composition including gold powder is applied onto the flexible portion.

The method below is, however, more preferable since it gives an opaque more effectively, and gives clearer X-ray photographs.

(4) An inorganic material having the specific gravity of not less than 5, specifically not less than 8, is contained in the flexible portion.

In case of (4), any inorganic material with the specific gravity of not less than 8 may be used as long as the application thereof as a catheter in the human body is allowable. Some examples are gold, silver, platinum, tungsten, barium, zinc, tantalum, molybdenum, bismuth, iridium, and their oxides (e.g., bismuth tungstate, barium tungstate, bismuth subcarbonate oxide, and bismuth oxide), carbides, nitrides, and sulfides.

The size of the catheter of the invention is not specified, and the catheter of the invention may have any size according to the application region and function. Examples thereof include those wherein the size is identical from the torque transmitting portion to the flexible portion, those wherein the catheter is gradually taper from the torque transmitting portion to the flexible portion, those wherein the torque transmitting portion has the identical size and the flexible portion tapers, those wherein only the tip, i.e., 1 through 5 mm from the free end, of the flexible portion is thinner than the rest, or the like.

The catheter of the invention may have any sectional structure. It may be either a single lumen tube or multi-lumen tube. The multi-lumen tube has functional devices such as image guides, light guides, flash channels, and laser fibers in the corresponding holes, which may be inserted before or after insertion of the catheter.

Manufacture of the catheter of the invention, which has the structure and is made of the material as described above, is now explained.

Some methods for manufacturing the catheter having rigidity on its torque transmitting portion and both rigidity and flexibility on its flexible portion are stated.

(1) A rigid torque transmitting portion and a flexible portion with appropriate flexibility are separately manufactured. Then, the two portions are joined to each other with an adhesive or adhered to each other with heat.

(2) The organic polymer composition of a small diameter, a material for the catheter, is molded by extrusion or another method.
Appropriate post-treatment is then respectively made on the flexible portion and the torque transmitting portion so as to give the required flexibility and rigidity to them. The following is an improved method disclosed in Canadian Patent No. 093071.

(3) A first plastic material having required physical properties such as flexibility for composing the flexible portion which makes the post-treatment unnecessary is inserted into a first extruder. A second plastic material having required physical properties such as rigidity for composing the torque transmitting portion is inserted into a second extruder. Firstly, only the first plastic material is extruded. After a certain time period, the second extruder starts extrusion in a manner wherein the flow of the first extruder is gradually reduced in proportion to increase of that of the second extruder, to give a catheter by extrusion.

(4) A material block composing the torque transmitting portion and that composing the flexible portion are inserted into an extruder and the flexible portion and the torque transmitting portion are fusion-extruded in sequence.

The method (4) is especially preferable since catheters manufactured according thereto have less structural or property deficiencies. In the method (3) with two extruders, the composition of the extruded material is gradually changed. Namely, the ratio of the material for the flexible portion to that for the torque transmitting portion is successively changed. On the other hand, the method (4) uses only one extruder. The material for the flexible portion and that for the torque transmitting portion are separately, though in contact with each other, inserted into an extruder and successively extruded as described later according to FIGS. 8 and 9.

One specific feature of the catheter of the invention is its flexible portion, which holds rigidity sufficient for smooth insertion before insertion and develops flexibility after insertion by the body heat. The catheter of the invention has a structure and functions corresponding to the applied region such as circulatory systems such as coronary arteries, respiratory systems, digestive systems, urinary systems, generative systems, sensory systems, spines, and joints, and purposes such as treatment and diagnosis.

The shape-memory catheter, which has the specific glass transition temperature and elastic modulus and expands to a larger diameter after insertion, is useful for effectively injecting and evacuating fluids or opening the target region. Specifically, catheters with the flexible portion restored to a larger diameter are suitable for urinary and generative systems. When a conventional catheter is inserted into ureters or uriniferous tubules connected thereto, it often touches the wall of the ureters to cause severe pain. The catheter of the invention, however, causes less pain since the flexible portion is maintained narrow during insertion and hardly touches the wall of the ureters. When the catheter is drawn out, it does not cause acute pains although the flexible portion is restored to a larger diameter, since the body heat has given appropriate flexibility to the flexible portion and the edge of the portion does not hurt the wall during pulling-out. The catheter of the invention is also applicable to the uterus for preventing undesirable amniorrhexis.

The shape-memory catheter which can be restored to a predetermined shape such as curve-shape or hook-shape is preferably used for cardiac, abdominal, and cerebral vessels. The catheter automatically changes the running direction when it is restored to a predetermined shape, thus allowing smooth and easy insertion or adjustment of the inserted direction or angle.

BRIEF DESCRIPTION OF THE DRAWINGS

FIGS. 1 (a) through (f) are various plan views of catheters embodying the invention, each having a specific glass transition temperature on a flexible portion and a torque transmitting portion, and graphs showing the relationship between the length of the catheter and glass transition temperature;

FIGS. 5 (a) through (c) show a catheter with a flexible portion made of shape-memory material.

THE BEST MODE FOR THE EMBODIMENT OF THE INVENTION

Figure 2:
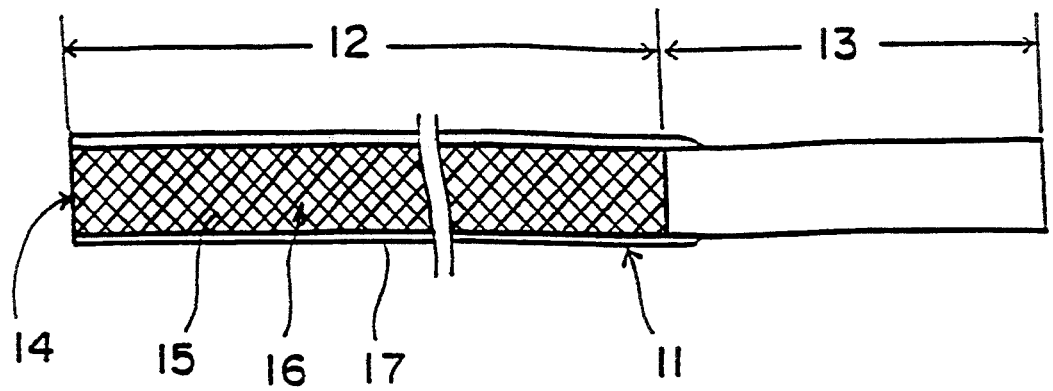
FIG. 2 is a partly-omitted schematic view showing a catheter including a torque transmitting portion reinforced with a braid of wires of flat rectangular cross section.

The catheter of the invention is now described according to the examples.

A catheter including a flexible portion with a specific glass transition temperature may have any known shape. Here, a catheter including a flexible portion and a torque transmitting portion both with a specific glass transition temperature is taken as an example, and the change of the glass transition temperature from the torque transmitting portion to the flexible portion is explained according to the degree of the change.

FIGS. 1(a) through (f) show various catheters and the change of the glass transition temperature ($T_g$) of each catheter. A catheter shown in FIG. 1(a) includes three portions $a_1$, $a_2$, and $a_3$, each having a different $T_g$. Here, $a_1$ and $a_3$ are a torque transmitting portion and a flexible portion respectively, and $a_2$ is middle part composed of both materials for $a_1$ and $a_2$. The glass transition temperature $T_g$ is constant in $a_1$, gradually decreases in $a_2$, and is constant at a lower value in $a_2$. The torque transmitting portion $a_1$ has $T_g$ and an elastic modulus sufficient for effective torque transmission, and $a_3$ has $T_g$ and an elastic modulus for giving appropriate flexibility after insertion by the body heat.

A catheter shown in FIG. 1(b) includes three portions $b_1$, $b_2$, and $b_3$, each having a different $T_g$. Here, $b_1$, $b_2$ and $b_3$ are torque transmitting portion, connection, and flexible portion, respectively as in FIG. 1(a). Although the glass transition temperature $T_g$ changes in a similar way to FIG. 1(a), $T_g$ gradually decreases in In a catheter shown in FIG. 1(c), the torque transmitting portion $c_1$ has a constant glass transition temperature $T_g$. $T_g$ decreases stepwise through the flexible portion $c_3$ to $c_5$. Here, $c_2$ is a middle part between the torque transmitting portion $c_1$ and the flexible portion $c_3$, and $c_4$ is a middle part between the two flexible portions $c_3$ and $c_5$.

A catheter shown in FIG. 1(d) has $T_g$ decreased substantially successively and gradually. Here, $d_1$ through $d_3$, $d_5$ through $d_7$, and $d_4$ correspond to a torque transmitting portion, a flexible portion, and a connection therebetween, respectively. The glass transition temperature $T_g$ decreases stepwise through the torque transmitting portion $d_1$ to $d_3$ with a middle part $d_2$ being a border therebetween and the flexible portion $d_5$ to $d_7$ similarly with the middle part do being a border therebetween.

In a catheter shown in FIG. 1(e), the torque transmitting portion $e_1$ is reinforced with a braid of wires of flat rectangular cross section and has a constant $T_g$. The temperature $T_g$ gradually decreases in the flexible portion $e_2$.

In a catheter shown in FIG. 1(f), the torque transmitting portion $f_1$ is reinforced with a coil of wires of flat rectangular cross section. $T_g$ decreases stepwise through the flexible portion $f_2$ to $f_4$ in a similar manner as in FIG. 1(c).

Figure 3:
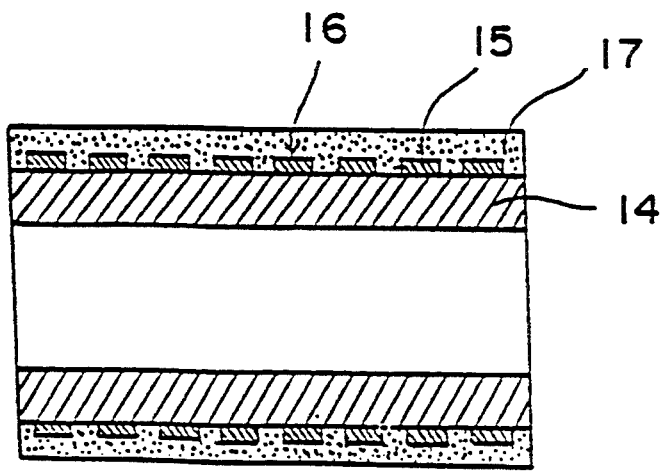
FIG. 3 is a longitudinal cross sectional view of the torque transmitting portion of the catheter of FIG. 2.

A catheter 11 shown in FIGS. 2 and 3 corresponds to that in FIG. 1(e) and has a torque transmitting portion 12 and a flexible portion 13. The torque transmitting portion 12 includes a tube 14 composed of organic polymers which may have the same or different glass transition temperature as that of the flexible portion 13, a metal reinforcement or a braid 16 composed of flat rectangular wires 15 covering the tube 14, and a resin coating 17 applied onto the metal reinforcement 16. The resin coating 17 covers the whole metal reinforcement 16 to the flexible portion 13.

Figure 4:
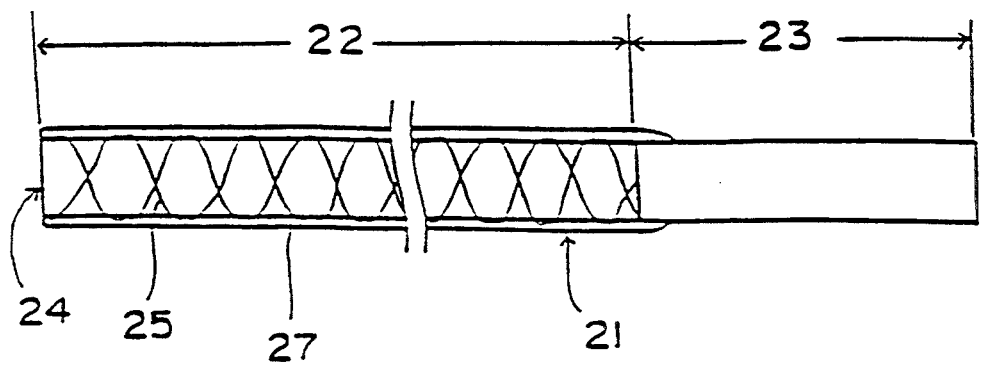
FIG. 4 is a partly-omitted schematic view showing a catheter including a torque transmitting portion reinforced with a coil of wires of flat rectangular cross section.

A catheter 21 shown in FIG. 4 corresponds to that in FIG. 1(f) and has a torque transmitting portion 22 including a tube 24 of a structure similar to the tube 14 of FIG. 2 reinforced with a coil of flat rectangular wires 25 wound at a certain pitch, and a resin coating 27 applied onto the coil 25. The flat rectangular wires 25 are wound in two opposite directions to have an angle of approximately 54° to the axis of the tube 24.

Figure 5A:
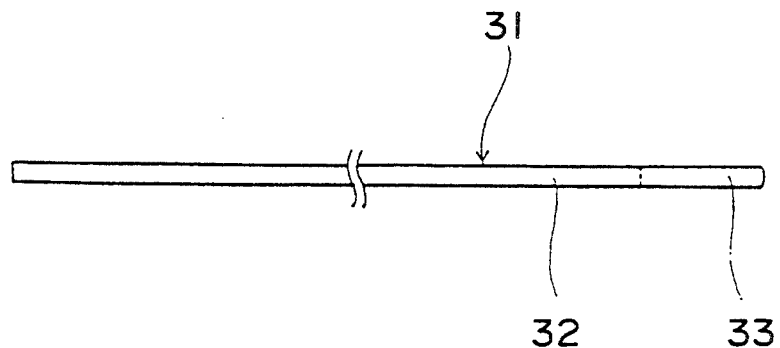
FIG. 5(a) is a partly-omitted schematic view showing a catheter before restoration.
Figure 5B:
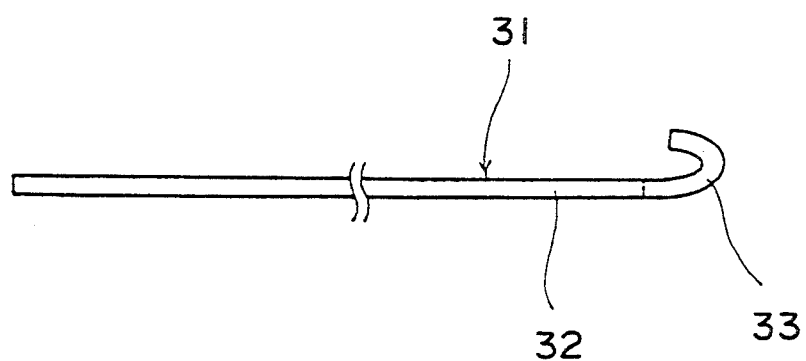
FIG. 5(b) is a partly-omitted schematic view showing the catheter of FIG. 5(a) restored to a predetermined shape by the body heat.

A catheter 31 shown in FIG. 5(a) has a shape-memory flexible portion 33. A torque transmitting portion 32 maintains sufficient torque transmitting ability even when it is warmed by the body heat. The flexible portion 33 has rigidity before insertion and appropriate flexibility after insertion. FIG. 5(b) shows the flexible portion 33 in FIG. 5(a) restored to a hook-shape by the body heat.

Since the flexible portion 33 has proper rigidity before insertion into vessels and organs without being sufficiently warmed by the body heat, the catheter 31 is smoothly and easily inserted to reach a position where the inserted direction and angle are changed and adjusted. By the time the flexible portion reaches the position for adjustment, it has been sufficiently warmed by the body heat, develops appropriate flexibility and is restored to a predetermined shape with predetermined angle and direction while the torque transmitting portion 32 still holds sufficient torque transmitting ability, thereby enabling easy change of direction of the flexible portion 33 and smooth insertion of catheter 31 into the target region.

Figure 5C:
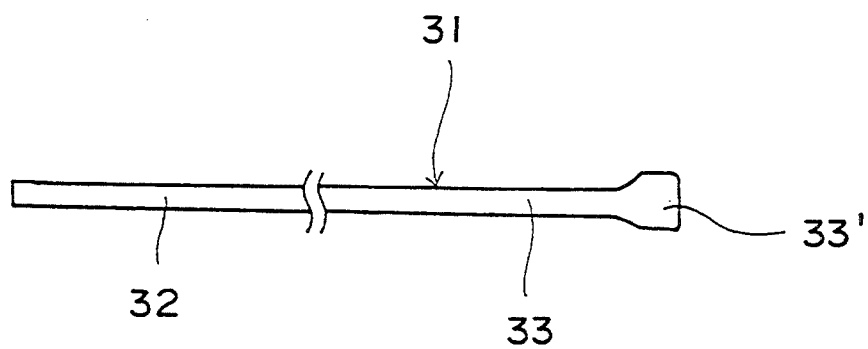
FIG. 5(c) is a partly-omitted schematic view showing the catheter restored to a larger diameter by the body heat.

The catheter 31 shown in FIG. 5(c) has the same structure as that shown in FIG. 5(a) before insertion. The flexible portion 33 includes a shape-memory end 33', which is predetermined to be restored to a larger diameter than the rest of the shape-memory portion after insertion. The diameter of the catheter of FIG. 5(c) is of a small diameter and substantially the same throughout the length (including the shape-memory end 33') before being warmed by the body heat. Since only the end 33' of the flexible portion 33 is restored to a wider diameter, the catheter 31 thus constructed is suitable for urinary and generative systems. It is especially effective for preventing undesirable amniorrhexis.

The catheter 31 shown in FIG. 5(b) or 5(c) is manufactured as follows. The torque transmitting portion 32 and the flexible portion 33 are formed in linear shape by extrusion or another method using the materials for each portion. The flexible portion 33 is heated to a temperature as high as cohesion temperature of hard segments in the constituent, given a desired shape (memorized shape), and cooled to a temperature a little higher than the glass transition temperature while maintaining the shape. The flexible portion 33 is then re-formed to its original linear shape at said temperature and cooled at room temperature.

Figure 6:
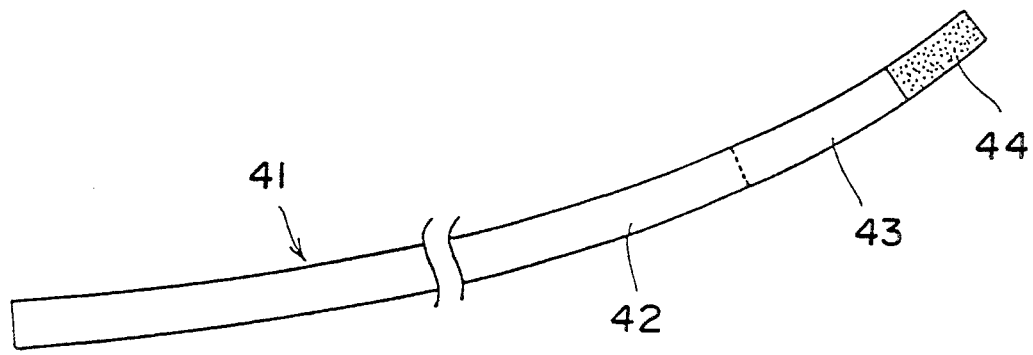
FIG. 6 is a partly-omitted schematic view showing a catheter including a flexible portion containing a material opaque to X-ray.

FIG. 6 shows a catheter 41 with a material opaque to X-ray. The catheter 41 includes a torque transmitting portion 42, a flexible portion 43, and an insertion end 44 including a material opaque to X-ray. The end 44 includes an inorganic material of high specific gravity for giving a fine opaque. The whole torque transmitting portion 42 and the flexible portion 43 may also contain the material opaque to X-ray.

Figure 7A:
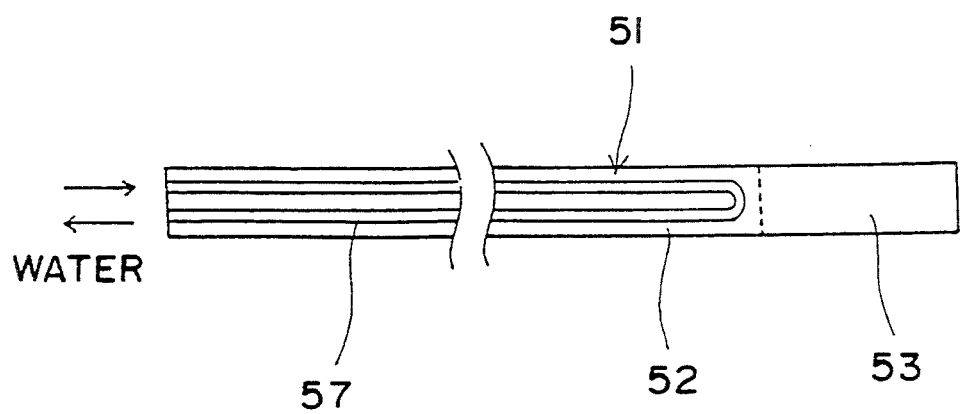
FIG. 7(a) and (b) show a catheter with a temperature control mechanism on a torque transmitting portion, wherein (a) is a partly-omitted longitudinal cross sectional view and (b) is a transverse cross sectional view of the torque transmitting portion.
Figure 7B:
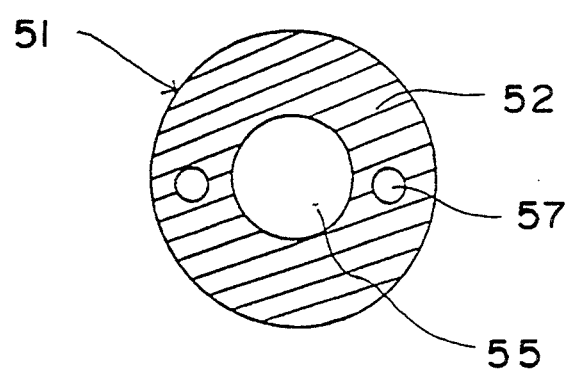

FIGS. 7 (a) and (b) show a catheter 51 with a temperature control mechanism. A torque transmitting portion 52 has water paths 57 for circulating cooling water to maintain the torque transmitting portion 52 at a constant temperature as well as a main path 55 for conducting various operations as a catheter. Water is circulated through the water path 57 during insertion, thus preventing the torque transmitting portion 52 to be undesirably warmed by the body heat. The flexible portion is shown at 53.

Manufacture of catheters of the invention based on the method (4) is described in detail in the following.

Figure 8:
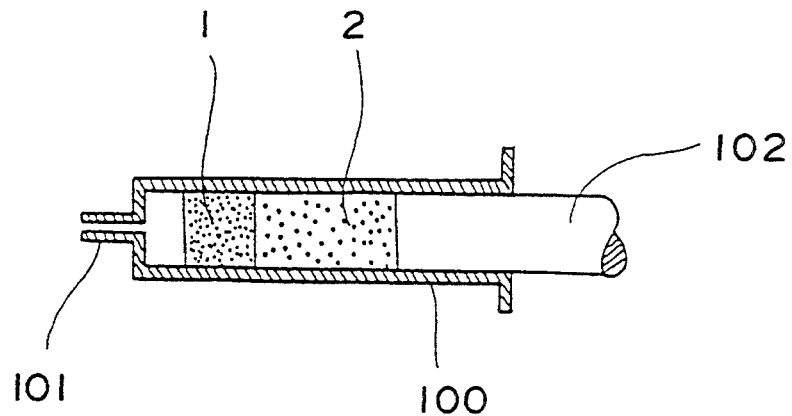
FIG. 8 is a schematic view showing a method for manufacturing a catheter of the invention based on the method (4)

FIG. 8 shows extrusion molding of one catheter. A block of material 1 for composing a flexible portion (organic polymer with a lower glass transition temperature, hereinafter referred to as flexible portion material) and a block of material 2 for composing a torque transmitting portion (organic polymer with a higher glass transition temperature, hereinafter referred to as torque transmitting portion material) are inserted into a cylinder 100. The cylinder 100 is heated to sufficiently high temperatures, and thereby the material blocks 1 and 2 melted. The materials 1 and 2 are successively extruded from an opening of a smaller diameter 101 with a plunger 102 installed on one end of the cylinder 100 to form a catheter of a small diameter.

Figure 9:
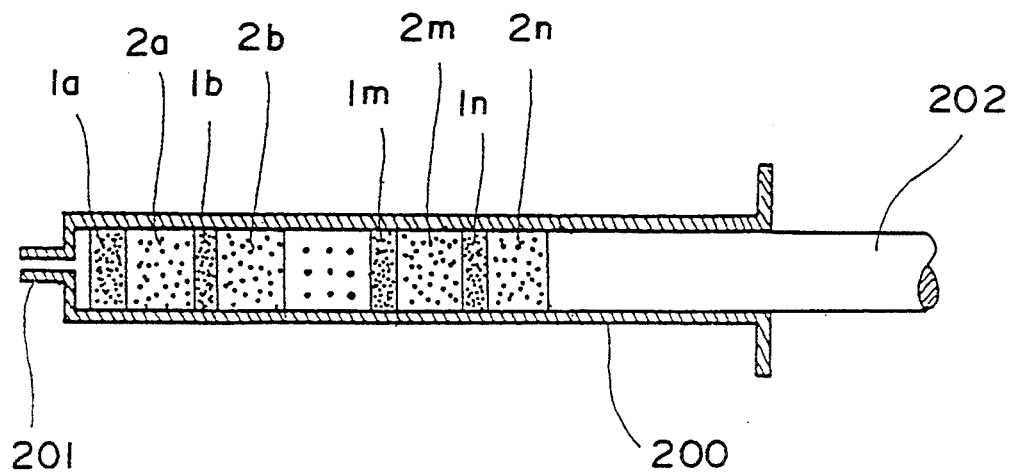
FIG. 9 is a schematic view showing another method for manufacturing a catheter of the invention based on the method (4).

FIG. 9 shows manufacture process for continuously molding plural catheters by extrusion. Blocks of flexible portion material 1a, 1b, . . . . . , 1m, and 1n and torque transmitting material blocks 2a, 2b, . . . . . . . , 2m, and 2n for composing plural catheters are inserted alternately in cylinder 200. The materials are successively extruded from an opening of a smaller diameter 201 with a plunger 202 installed on one end of the cylinder 200 to form a long integral tube for plural catheters of small diameter. The tube is then cut into a desirable number of catheters, and further into catheters of a desirable length.

Some examples of the catheters according to the invention and comparison example are shown below to show the marked achievement of the invention. Table 1 shows materials used in examples and comparison example and their properties. Examples 1 through 5; and Comparison Example 1

Single lumen catheters with structure and dimensions shown in Table 2 were manufactured. The length of each catheter was 150 cm. Both flexible portion and torque transmitting portion had 1.40 mm of diameter and 2.35 mm of outer diameter.

Catheters of Examples 1 through 4 are composed of two or more materials selected from those shown in Table 1. They were fusion extrusion-molded at a temperature of 185° C. according to manufacturing process shown in FIG. 8. Although each catheter has a middle part (3 cm on the average) in which the both materials are mixed and fusion-connected, the lengths shown in Table 2 are based on the assumption that the middle part does not exist (i.e., the length of each portion includes half the length of the connection). When the flexible portion is made of more than one material, the upper column shows the material for the end of the flexible portion of the catheter.

A catheter of Example 5 includes a torque transmitting tube, which is composed of material B and reinforced with a braid of flat rectangular wires SUS 304 (thickness: 25 μm; wire width: 110 μm). The braid (outer diameter: 1.95 mm; inner diameter: 1.8 mm; density of flat rectangular wires: 16/circumference; inclination angle of each flat rectangular wire to the axis of catheter: 45 degrees; length: 130 cm) was placed approximately in the center of the thickness of the tube. A flexible tube composed of material B solely was separately molded by extrusion. Both the torque transmitting tube and the flexible tube (outer diameter: 2.35 mm; inner diameter: 1.40 mm, for both) were then adhered with heat.

Comparison Example 1 is a tube composed of material B solely throughout the whole length of 150 cm.

Torque transmitting ability was measured for each catheter according to the following method. Table 2 shows the results. Torque transmitting ability:

Each catheter was inserted into a U-shaped tube composed of SUS (longitudinal length: 122 cm; transverse length: 10 cm; radius of curvature: approximately 5 cm; total length: 140 cm; inner diameter: 3 mm) on a table to project the end of the flexible portion of the catheter by 1 to 2 mm from an opening of the tube. Then the space between the inserted catheter and the U-shaped tube was filled with saline at 36.5° C. and the room was kept at 36.5° C. After the catheter was kept standing for 5 minutes, the end of the torque transmitting portion of the catheter projected from the other opening of the U-shaped tube was twisted by 180 degrees. The rotational angle of the insertion end of the flexible portion was measured.

TABLE 1

| | Material | | | | | | | | |
|---|---|---|---|---|---|---|---|---|---|
| | A | B | C | D | E | F | G | H | I |
| Polyurethane-1 (Note 1) | 100 | — | — | 20 | 60 | 70 | 80 | — | — |
| Polyurethane-2 (Note 2) | — | 100 | — | — | — | — | — | 20 | — |
| Polyurethane-3 (Note 3) | — | — | 100 | — | — | — | — | — | 20 |
| Liquid crystal polymer (Note 4) | — | — | — | 80 | 40 | 30 | 20 | 80 | 80 |
| Glass transition temperature (°C.) | 33 | 36 | 42 | >50 | 42 | 40 | 37 | >50 | >50 |
| Elastic modulus (kgf/mm$^2$) | | | | | | | | | |
| 20° C. | 150 | 107 | 135 | 126 | 58 | 43 | 34 | 130 | 140 |
| 37° C. | 1.1 | 0.9 | 7.0 | 71 | 26 | 14 | 1.6 | 70 | 100 |

(Note 1): Ether polyurethane produced by MITSUBISHI JUKOGYO KABUSHIKI KAISHA (Trade name: DIARY MM3301, Average molecular weight: 3.8 × 10$^5$, Crystallinity: 5.6 w%)
(Note 2): Ether polyurethane produced by MITSUBISHI JUKOGYO KABUSHIKI KAISHA (Trade name: DIARY MM3611, Average molecular weight: 3.2 × 10$^5$, Crystallinity: 45.0 w%)
(Note 3): Ether polyurethane produced by MITSUBISHI JUKOGYO KABUSHIKI KAISHA (Trade name: DIARY MM4221, Average molecular weight: 4.2 × 10$^5$, Crystallinity: 48.0 w%)
(Note 4): Non-aromatic liquid crystal polymer producted by MITSUBISHI CHEMICAL INDUSTRIES (Trade name: E 310)

TABLE 2

| | Example 1 | Example 2 | Example 3 | Example 4 | Example 5 | Comp. Ex. 1 |
|---|---|---|---|---|---|---|
| Structure of catheter | | | | | | |
| Flexible portion | Material-B length: 20 cm | Material-F length: 20 cm | Material-A length: 20 cm Material-C length: 30 cm | Material-G length: 10 cm Material-E length: 40 cm | Material-B length: 20 cm | Material-B length: 20 cm |
| Torque transmitting portion | Material-H length: 130 cm | Material-D length: 130 cm | Material-I length: 100 cm | Material-H length: 100 cm | That made of Material-B with a flat wire net length: 130 cm | Material-B length: 130 cm |
| Torque transmitting ability (degrees) Torque transmitting angle | 60 | 90 | 45 | 48 | 135 | 0 |

Effects of the metal reinforcements used in the invention are shown below.

Three tubes, i.e., tube 1, tube 2, and tube 3, were prepared. Tube 1 (outer diameter: 2.65 mm; inner diameter: 1.65 mm) was made of polyurethane solely (Trade name: Petesen 2363 55DE; Shore hardness: 55 by MD Kasei Ltd.). Tube 2 (the same composition as tube 1) was reinforced with a braid (outer diameter: 2.3 mm; inner diameter: 2.0 mm; density of the wires: 16/circumference; inclination angle of each wire to the axis of the catheter: 45 degrees) of SUS 304 round wires (outer diameter: 60 μm) placed approximately in the center of the thickness of the tube. Tube 3 (the same composition as tube 1) was reinforced with a braid (outer diameter: 2.2 mm; inner diameter: 2.1 mm; density of the wires: 16/circumference; inclination angle of each wire to the axis of the catheter: 45 degrees) of SUS 304 flat rectangular wires (thickness: 25 μm, wire width 110 μm) instead of the round wires of tube 2.

The transverse elastic modulus (torsion: kgf/mm$^2$) and longitudinal elastic modulus (bending: kgf/mm$^2$) were 10 and 10 for tube 1, 20 and 40 for tube 2 and 30 and 30 for tube 3, respectively. The tubes reinforced with metal wires generally had greater elastic modulus than the tube without reinforcements. The tube 3 reinforced with flat rectangular wires showed higher transverse elastic modulus and lower longitudinal elastic modulus than the tube 2 reinforced with round wires. It means that the tube 3 had favorable flexibility while maintaining better torque transmitting ability.

We claim:

1. A catheter for insertion into one of a human and an animal body comprising a torque transmitting tubular section (a) which has rigidity sufficient for torque transmission, a flexible tubular section (b) made of a material having a glass transition temperature between 21.5° C. and 51.5° C. and a middle tubular section (c) arranged between said section (a) and said section (b) having a glass transition temperature between that of said section (a) and that of said section (b), wherein said section (b) has a length of 5–500 mm, said section (a) has a length greater than said section (b), and said section (a) maintains its rigidity for torque transmission after insertion into said body.

2. A catheter as claimed in claim 1, wherein said section (b) is made of polyurethane.

3. A catheter as claimed in claim 1, wherein said section (a) is composed of a material having a glass transition temperature at least 10° C. higher than a temperature of said body.

4. The catheter as claimed in claim 1, wherein said torque transmitting section (a) includes means for controlling temperature of said section (a).

5. A catheter as claimed in claim 1, wherein said section (a) is made of a material more rigid than said section (b).

6. A catheter as claimed in claim 1, wherein the section (a) includes an organic polymer layer and a metal reinforcement.

7. A catheter as claimed in claim 6 wherein said metal reinforcement is a braid of flat rectangular wires.

8. The catheter as claimed in claim 1, wherein said section (b) includes a first part and a second part respectively having different glass transition temperatures.

9. The catheter as claimed in claim 8, wherein said section (a) includes an organic polymer layer and a metal reinforcement.

10. The catheter as claimed in claim 8, wherein said section (a) includes means for controlling temperature of said section (a).

11. The catheter as claimed in claim 8, wherein said section (a) includes a first part and a second part respectively having different glass transition temperatures.

12. The catheter as claimed in claim 11, including means for controlling temperature of said section (a).

13. The catheter as claimed in claim 12, wherein said tubular section (a) has a glass transition temperature of at least 10° C. higher than a temperature of said body.

14. A catheter as claimed in claim 1, wherein said section (a) has a glass transition temperature of at least 46.5° C.

15. A catheter comprising a torque transmitting section (a), a flexible tubular section (b), and a middle tubular section arranged between said section (a) and said section (b), said flexible section (b) having a glass transition temperature between 21.5° C. and 51.5° C. and lower than that of said torque transmitting section (a), and said middle section (c) having a glass transition temperature between that of section (a) and that of section (b).

16. The catheter as claimed in claim 15, wherein said section (a) has a glass transition temperature of at least 46.5° C.

* * * * *